US012514986B1

(12) United States Patent
Coyne, III et al.

(10) Patent No.: US 12,514,986 B1
(45) Date of Patent: Jan. 6, 2026

(54) MEDICAMENT DELIVERY DEVICE

(71) Applicant: Genzyme Corporation, Cambridge, MA (US)

(72) Inventors: Martin Michael Coyne, III, Boonton, NJ (US); Madeleine Hayden Anderson, Boonton, NJ (US); Katherine Ford Brigham, Boonton, NJ (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/960,631

(22) Filed: Nov. 26, 2024

(51) Int. Cl.
*A61M 5/315* (2006.01)
*A61M 5/31* (2006.01)

(52) U.S. Cl.
CPC ........ *A61M 5/3155* (2013.01); *A61M 5/3135* (2013.01); *A61M 5/31528* (2013.01); *A61M 5/31551* (2013.01)

(58) Field of Classification Search
CPC .. A61M 2005/3125; A61M 2005/3126; A61M 5/315; A61M 5/31511; A61M 5/31525; A61M 5/31526; A61M 5/31528; A61M 5/31533; A61M 5/31548; A61M 5/3155; A61M 5/31551; A61M 2005/3114; A61M 5/3135
See application file for complete search history.

(56) References Cited

U.S. PATENT DOCUMENTS

| | | | | |
|---|---|---|---|---|
| 7,976,510 B2 * | 7/2011 | Janish | ................ | A61M 5/31511 604/218 |
| 10,149,948 B2 * | 12/2018 | Schenker | ................ | A61M 5/20 |
| 10,213,556 B2 * | 2/2019 | Young | ............... | A61M 5/31528 |
| 2022/0233779 A1 * | 7/2022 | Shabudin | ........... | A61M 5/31511 |

FOREIGN PATENT DOCUMENTS

WO WO-2010149396 A1 * 12/2010 .............. A61M 5/20

OTHER PUBLICATIONS

Needle-based injection systems for medical use requirements and test methods, Part 1: Needle injection systems, ISO 11608 1:2014(E), Third Edition, Switzerland, ISO, Dec. 15, 2014, pp. 1-13.

(Continued)

*Primary Examiner* — Shefali D Patel
(74) *Attorney, Agent, or Firm* — Fish & Richardson P.C.

(57) ABSTRACT

A medicament delivery device comprises a syringe body configured to receive a medicament. The syringe body comprises a distal end and a proximal end, a plunger located in and moveable relative to the syringe body, and a plunger rod assembly extending from the proximal end of the syringe body and configured to move the plunger longitudinally within the syringe body. The plunger rod assembly comprises a plunger barrel and a plunger rod. The plunger barrel contacts the plunger and is configured to cooperate with the plunger rod, which is moveable relative to the plunger barrel from a first position, in which the plunger rod is maximally extended from the plunger barrel, to a second position, in which the plunger rod is distally away from the first position, to set a specific dose of the medicament to be (Continued)

delivered less than an amount of the medicament in the syringe body.

21 Claims, 6 Drawing Sheets

(56) References Cited

OTHER PUBLICATIONS

U.S. Appl. No. 18/960,437, filed Nov. 26, 2024, Haiming Wu.
U.S. Appl. No. 18/960,517, filed Nov. 26, 2024, Alejandra Linares Martinez.
U.S. Appl. No. 18/960,617, filed Nov. 26, 2024, Haiming Wu.
U.S. Appl. No. 18/960,725, filed Nov. 26, 2024, Martin Michael Coyne III.

* cited by examiner

MEDICAMENT DELIVERY DEVICE

TECHNICAL FIELD

The present application relates to a medicament delivery device and a method of setting a dose for delivery using a medicament delivery device.

BACKGROUND

Administration of medicament in a home setting offers benefits for both patients and the healthcare system. Visits to a healthcare setting for a patient are frequent and can be lengthy when taking into account commute times, waiting times, and delays. For these reasons and the added comfort of one's home, patients often prefer to receive therapy in the homes, wherever possible. This provides autonomy and improved convenience, whilst also reducing the overall burden on the healthcare system.

Medicament is often prefilled in a reservoir, such as a flexible IV container or a rigid pre-filled syringe or cartridge for direct administration or subsequent addition to an IV bag with a common commodity solution. Where all patients are to receive a fixed dose, the volume may be pre-filled into a single reservoir of suitable size and stored in a stable liquid formulation.

However, this is not always the case. In some instances, a vial may be used with either a liquid or lyophilised presentation. Preparation of these medicaments in a health-care setting are undertaken in sterile environments and governed by specific guidelines. Even under these conditions, preparation of these medicaments is time consuming and error prone. Preparation also usually has to take place on a patient-specific basis at the point and time of delivery.

In the home setting, the process controls may not be in place and the admixture steps themselves may be alien and confusing to a patient. Furthermore, the dosing required for each patient may be different, depending on body weight for example, and the dosing scheme may require different amounts of medicament to be delivered in subsequent infusions. In addition, the medicament is often provided in large quantities and in multiple packaged vials, which can take up large volumes of space, and sometimes required special conditions, such as being kept in a refrigerator or freezer.

SUMMARY

In some aspects, the present disclosure relates to an advantageous medicament delivery device comprising a syringe body configured to receive a medicament therein, the syringe body comprising a distal end and a proximal end, a plunger located in and moveable relative to the syringe body, and a plunger rod assembly extending from the proximal end of the syringe body and configured to move the plunger longitudinally within the syringe body, wherein the plunger rod assembly comprises a plunger barrel and a plunger rod, wherein the plunger barrel is in contact with the plunger and configured to cooperate with the plunger rod, wherein the plunger rod is moveable relative to the plunger barrel from a first position, in which the plunger rod is maximally extended from the plunger barrel, to a second position, in which the plunger rod is in a distal position relative to the first position, to set a specific dose of medicament to be delivered that is less than the amount of medicament received in the syringe body.

Advantageously, the medicament delivery device of the present disclosure enables a patient to easily and instinctively set a dose of medicament to be self-administered in a home setting. In addition, movement of the plunger rod relative to the plunger barrel reduces the overall length of the medicament delivery device making the step of delivering the medicament easily to execute.

In some embodiments, the plunger rod assembly may be moveable between a distal position and a proximal position, and wherein the plunger rod may be moveable in the distal direction from its first position to a second position when the plunger rod assembly is in the proximal position.

Thus, the plunger rod assembly may be used to draw up a full syringe of medicament, and then the exact dose can be determined by moving the plunger rod relative to the plunger barrel. Moving the plunger rod when the plunger rod assembly is in the proximal position ensures that a full dose may be delivered and ensures all medicament drawn up is retained in the syringe during dose setting.

In some embodiments, the plunger rod may be rotatable relative to the plunger barrel to move the plunger rod from its first position to its second position.

In some embodiments, the plunger rod may comprise a first thread and the plunger barrel comprises a second thread, the first thread and second thread being configured to cooperate such that when the plunger rod is rotated relative to the plunger barrel, the plunger rod translates distally relative to the plunger barrel.

Advantageously, rotation of the plunger rod relative to the plunger barrel allows for large rotational inputs to be transformed into accurate translational movements of the plunger barrel. Thus, large rotations can be transformed into small longitudinal movements to aid accuracy of dose setting for those of reduced dexterity or control.

In some embodiments, an inner surface of the syringe body may comprise a first cooperating feature configured to cooperate with a second cooperating feature on the plunger barrel to prevent relative rotational movement between the plunger barrel and the syringe body.

Thus, dose setting using the device of the present disclosure can be performed accurately as the torque applied to the plunger barrel from the plunger rod cannot rotate the plunger barrel.

In some embodiments, the plunger barrel may comprise an internal bore configured to receive at least a portion of the plunger rod, at least a section of the internal bore comprising the second thread configured to engage the first thread on the plunger rod.

In some embodiments, the second thread may extend along the whole length of the internal bore.

Advantageously, the longitudinal movement of the plunger rod relative to the plunger barrel can be accurately controlled to set a dose along the whole length of the plunger barrel.

In some embodiments, the second thread may extend along a proximal section of the length of the internal bore.

Advantageously, the second thread may cooperate with the length of the first thread and allows a simpler bore design in which further elements of a plunger rod may be accommodated.

In some embodiments, the plunger rod may comprise a shaft configured to be at least partially received in the internal bore of the plunger barrel, at least a portion of the outer surface of the shaft comprising the first thread configured to engage the second thread on the plunger barrel.

In some embodiments, the first thread may extend along the whole length of the shaft.

Advantageously, the longitudinal movement of the plunger rod relative to the plunger barrel can be accurately controlled to set a dose along the whole length of the plunger rod.

In some embodiments, the first thread may extend along a proximal portion of the length of the shaft and the distal portion of shaft may comprise a threadless surface.

Advantageously, the threadless surface may be configured to not engage or cooperate with a thread on the plunger barrel to allow for pure longitudinal movement of the plunger rod relative to the plunger barrel over a pre-defined distance. Thus, a portion of the dose setting step can be achieved much quicker compared to rotating the plunger rod relative to the plunger barrel.

In some embodiments, the distal end of the shaft may comprise a stop configured to abut a projection on the proximal end of the plunger barrel, the shaft and projection being configured to cooperate to prevent the plunger rod being removed from the plunger barrel.

In some embodiments, one of a shaft of the plunger rod and an internal bore of the plunger barrel may comprise a thread and the other of the shaft of the plunger rod and the internal bore of the plunger barrel may comprise a protrusion configured to cooperate with the thread.

Advantageously, the design of the cooperating plunger rod and plunger barrel may be simplified.

In some embodiments, the thread angle of the thread may vary along the length of the shaft of the plunger rod or the internal bore of the plunger barrel.

Advantageously, this allows for less rotations of the plunger rod to cause a larger change in dose. This is especially useful for small dosage regimes compared to the maximum volume capacity of the syringe.

In some embodiments, the shaft of the plunger rod may comprise a plurality of graduation marks configured to indicate to a user the size of the dose set based on the amount of distal movement of the plunger rod relative to the plunger barrel.

In some embodiments, the plunger barrel may comprise a window in which the graduation marking that indicates the size of the dose set is displayed.

Advantageously, the plurality of graduation marks enable a user to determine the size of the dose set to increase accuracy of the dose.

In some embodiments, the plunger barrel may comprise a finger extending into the window that points towards the graduation marking that indicates the size of the dose set shown in the window.

Advantageously, the finger enables the exact dose size to be more clearly indicated, which leads to an increase of the accuracy of the dose set.

In some embodiments, the plunger rod assembly may further comprise a ratchet mechanism configured to allow rotation of the plunger rod relative to the plunger barrel in a direction that results in movement of the plunger rod towards a second position and configured to prevent rotation of the plunger rod relative to the plunger barrel in a direction that results in movement of the plunger rod towards the first position.

Advantageously, the ratchet mechanism prevents re-use of the medicament delivery device.

In some embodiments, the plunger rod may comprise a head configured to abut the proximal end of the syringe body to limit the plunger rod assembly stroke such that a specified dose of medicament is dispensed when the plunger rod assembly is moved from its proximal position to its distal position.

In some embodiments, the plunger barrel may have a friction fit connection with the plunger.

Thus, torque applied to the plunger and plunger barrel by use of the device cannot cause the plunger to become disconnected from the plunger barrel.

In some embodiments, the distal end of the syringe body may comprise a connecting means for connecting a needle to the syringe body.

In some aspects, the present disclosure relates to an advantageous method of setting a dose of medicament in a medicament delivery device, the method comprising moving a plunger rod assembly in its first position from a distal position to a proximal position to draw medicament into a syringe body, rotating a plunger rod relative to a plunger barrel to move the plunger rod distally from a first position, in which the plunger rod is maximally extended from the plunger barrel, to a second position, in which a head of the plunger rod is positioned closer to the distal end of the syringe body, to set a specific dose of medicament to be delivered that is less than the amount of medicament that is received in the syringe body.

These and other aspects of the disclosure will be apparent from and elucidated with reference to the embodiments described hereinafter.

BRIEF DESCRIPTION OF THE DRAWINGS

Embodiments of the disclosure will now be described, by way of example only, with reference to the accompanying drawings, in which.

DETAILED DESCRIPTION

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 1 cP to about 50 cP. Consequently, a drug delivery device will often include a hollow needle ranging from about 25 to about 31 Gauge in size. Common sizes are 27 and 29 Gauge.

Figure 1:
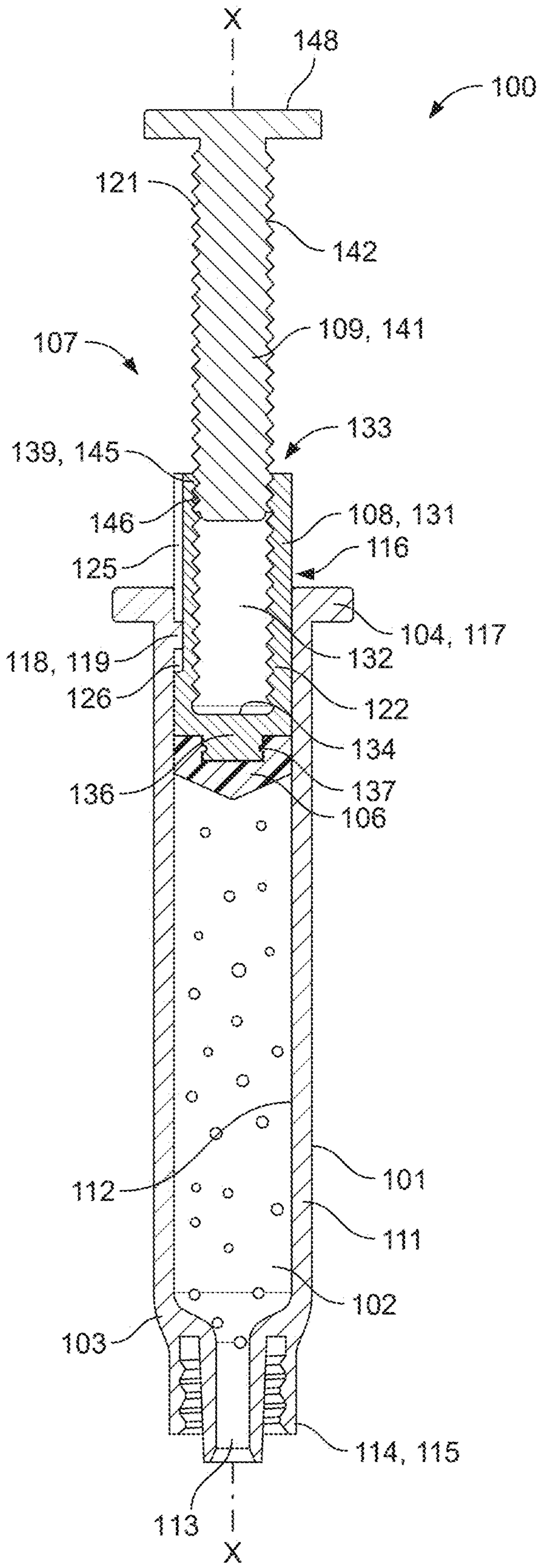
FIG. 1 shows a schematic cross-sectional side view of a medicament delivery device in the first and proximal position

Referring now to FIG. 1, a schematic cross-sectional side view of a medicament delivery device 100 is shown. The medicament delivery device 100 comprises a syringe body 101. The syringe body 101 is configured to receive a medicament 102 therein. The syringe body 101 comprises a distal end 103 and an opposing proximal end 104. The medicament delivery device 100 further comprises a plunger 106. The plunger 106 is located in the syringe body 101. The plunger is moveable relative to the syringe body 101.

The medicament delivery device 100 further comprises a plunger rod assembly 107. The plunger rod assembly 107 extends from the proximal end 104 of the syringe body 101. The plunger rod assembly 107 is configured to move the plunger 106 longitudinally within the syringe body 101.

The plunger rod assembly 107 comprises a plunger barrel 108 and a plunger rod 109. The plunger barrel 108 is in contact with the plunger 106. The plunger barrel 108 is configured to cooperate with the plunger rod 109. The plunger rod 109 is moveable relative to the plunger barrel 108 from a first position to a second position. In the first position, the plunger rod 109 is maximally extended from the plunger barrel 108. In the second position, the plunger rod 109 is in a distal position relative to the first position. The plunger rod 109 is moveable in the distal direction relative to the plunger barrel 108 to set a specific dose of medicament to be delivered. The specific set dose of medicament to be delivered is less than the amount of medicament received in the syringe body 101.

The syringe body 101 of the medicament delivery device 100 may be generally cylindrical. The syringe body 101 may be hollow. Therefore, the syringe body 101 may comprise a generally annular side wall 111. The plunger 106 may be located inside the hollow syringe body 101. The plunger 106 may be dimensioned so as to form a seal against an inner surface 112 of the syringe body 101. Thus, the plunger 106 may create a vacuum when moved proximally to draw medicament into the syringe body, when a distal end of the device 100 is placed into a medicament, and may force medicament out of the distal end of the device 100 when the plunger 106 is moved distally.

The distal end 103 of the syringe body 101 may be open ended. That is, the distal end 103 of the syringe body 101 may comprise a distal opening 113. The distal end 103 of the syringe body 101 may comprise a connecting means 114. The connecting means 114 may be configured to allow a needle (not shown) or other instrument to be connected to the medicament delivery device for delivering a medicament. The connecting means 114 may comprise, for example, but not limited to, a Luer lock 115 or a thread (not shown).

The proximal end 104 of the syringe body 101 may be open ended. That is, the proximal end of the syringe body 101 may comprise a proximal opening 116. The plunger rod assembly 107 may extend distally from the proximal end 104 of the syringe body 101. The proximal end 104 of the syringe body 101 may comprise a flange 117. The flange 117 may extend perpendicularly to the longitudinal axis X of the medicament delivery device 100. The flange 117 may extend radially outward. In some embodiments, the flange 118 may have an annular shape such that it extends about the proximal open end 104 of the syringe body 101. In some embodiments, the flange 117 may be at least one discrete radially extending projection. That is, in some embodiments, the flange 117 may not extend substantially in the circumferential direction.

The syringe body 101 may further comprise a first cooperating feature 118. The first cooperating feature 118 may be configured to cooperate with a second cooperating features on the plunger barrel 108, as explained in more detail hereinafter. The first cooperating feature 118 and the second cooperating feature may be configured to prevent relative rotational movement between the plunger barrel 108 and the syringe body 101.

The first cooperating feature 118 may comprise a protrusion 118. The protrusion 118 may extend from the inner surface 112 of the syringe body 101. The protrusion 118 may extend radially inwards, i.e. towards the longitudinal axis X of the medicament delivery device 100. The protrusion 118 may extend perpendicularly to the longitudinal axis X of the medicament delivery device 100. The protrusion 118 may be located at the proximal end 104 of the syringe body 101. That is, the protrusion 118 may be located proximate to the proximal opening 116 of the syringe body 101. The protrusion 118 may be configured to be located in a channel in the plunger barrel 108, as will be explained in more detail hereinafter.

The syringe body 101 may further comprise a stop 119. The stop 119 may be configured to limit proximal movement of the plunger barrel 108 relative to the syringe body 101. This may prevent the plunger rod assembly 107 from being removed from the syringe body 101. In some embodiments, the stop 119 may be formed by the first cooperating feature 118.

The plunger 106 may be connected to the plunger barrel 108. Therefore, movement of the lunger rod assembly 107 in the proximal and distal directions may cause the plunger 106 to move longitudinally with the plunger barrel 108 within the syringe body 101. The plunger 106 may be connected to the plunger barrel 108 by a friction fit. In alternative embodiments, the plunger 106 may be connected to the plunger barrel 108 via some other connection means, such as, for example, but not limited to, a threaded connection.

As previously disclosed, the plunger rod assembly 107 comprises a plunger rod barrel 108 and a plunger rod 109. The plunger rod assembly 107 may be moveable between a distal position and a proximal position, shown in FIG. 1.

When the plunger rod assembly 107 is in its distal position, substantially all of the plunger rod assembly 107 may be received within the syringe body 101. Furthermore, when the plunger rod assembly 107 is in its distal position, the plunger barrel 108 may be located within the syringe body 101 such that the plunger 106 is located proximate to or in abutment with the distal end 103 of the syringe body 101. That is, when the plunger rod assembly 107 is in its distal position, the plunger 106 may be located longitudinally adjacent to the connecting means 114 and/or immediately proximal to the distal opening 113.

When the plunger rod assembly 107 is in its proximal position, substantially all of the plunger rod assembly may extend proximally from the syringe body 101, as shown in FIG. 1. Furthermore, when the plunger rod assembly 107 is in its proximal position, the plunger barrel 108 may be located within the syringe body 101 such that the distal end of the plunger barrel 108 is located proximate the proximal opening 116 of the syringe body 101. When the plunger rod assembly 107 is in its proximal position, the plunger barrel 108 may have contacted the stop 119 of the syringe body 101 such that further proximal movement of the plunger rod assembly 107 is prevented.

When the plunger rod assembly 107 is in its proximal position, the plunger rod 109 may be moveable in the distal direction from its first position to a second position. That is, when the plunger rod assembly 107 is in its proximal position, the plunger rod 109 may be moveable from its maximally extended position in relation to the plunger barrel 108 to a more distal position, in which the plunger rod 109 extends by a smaller distance from the plunger barrel 108, as shown in FIG. 2.

Figure 2:
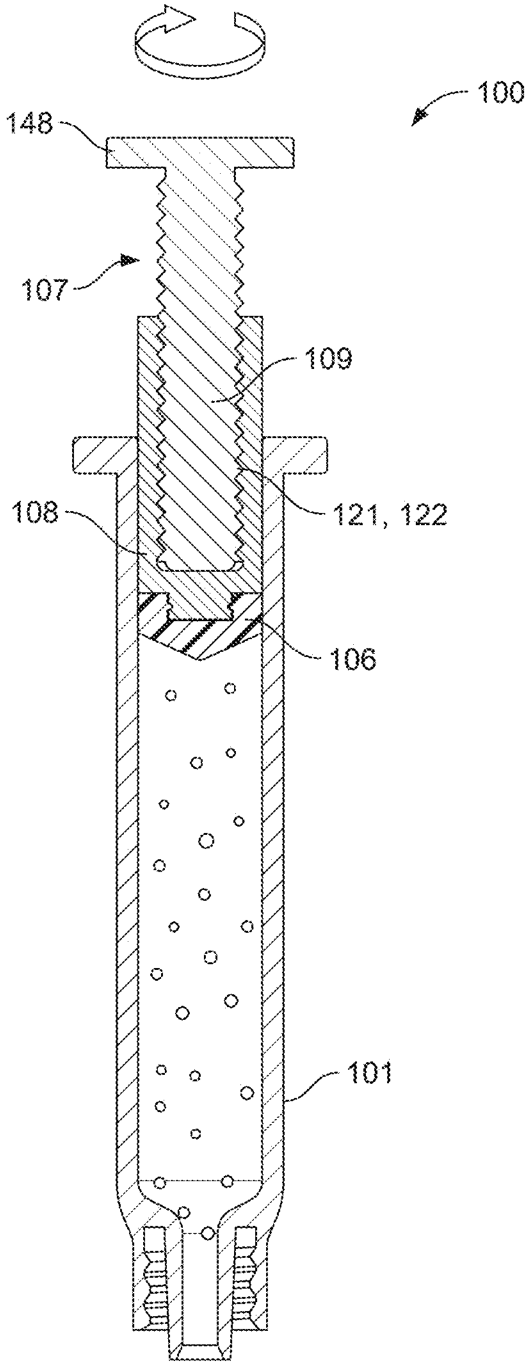
FIG. 2 shows a schematic cross-sectional side view of a medicament delivery device in the second and proximal position.

In some embodiments, the plunger rod 109 may be rotatable relative to the plunger barrel 108 to move the plunger rod 109 from its first position, shown in FIG. 1, to a distal, second position, shown in FIG. 2. It will be appreciated that the second position may be any position of the plunger rod 109 in which the plunger rod 109 is located in a more distal position relative to the plunger barrel 108 when compared to the location of the plunger rod 109 relative to the plunger barrel 108 in the first position.

The larger the difference between the first position and the second position set by a user, the smaller the dose of medicament is that can be delivered to a patient. That is, substantially the full contents of the syringe body, i.e. medicament, can be delivered to a patient when the plunger rod 109 is in its first maximally extended position. However, distal movement of the plunger rod 109 relative to the plunger barrel 108 effective reduces the stroke length of the plunger rod assembly 107. Therefore, the further the plunger rod 109 is moved in the distal direction from the first position, i.e. the more distal the second position is, the smaller the amount of medicament that can be dispensed from the medicament delivery device 100, as will be explained in more detail hereinafter.

The plunger rod 109 may comprise a first thread 121. The plunger barrel 108 may comprise a second thread 122. The first thread 121 and second thread 122 may be configured to cooperate such that when the plunger rod 109 is rotated relative to the plunger barrel 108, the plunger rod 109 also translates longitudinally relative to the plunger barrel 108. The plunger rod 109 may be rotated in a first direction relative to the plunger barrel 108 to cause the plunger rod 109 to translate in the distal direction relative to the plunger barrel 108.

The plunger barrel 108 may be generally cylindrical. The plunger barrel 108 may comprise a second cooperating feature 125. The second cooperating feature 125 may be configured to cooperate with the first cooperating feature 118 on the inner surface 112 of the syringe body 101. The first and second cooperating features 118, 125 may engage to prevent relative rotational movement between the plunger barrel 108 and the syringe body 101. Thus, when a user rotates the plunger rod 109, the plunger barrel 108 is prevented from rotating by its engagement with the syringe body 101.

The second cooperating feature 125 may comprise a guide channel 125. The guide channel 125 may extend along an exterior surface of the plunger barrel 108. The guide channel 125 may extend parallel to the longitudinal axis X of the medicament delivery device 100. The guide channel 125 may comprise a stop 126 in the form of an end wall. The stop 126 may be configured to abut the stop 119 of the syringe body 101 to prevent the plunger rod assembly 107 being removed from the syringe body 101. The protrusion 118 of the first cooperating feature on the syringe body 101 may be located in the guide channel 125 of the plunger barrel 108. Thus, the protrusion 118 located in the channel 125 prevents rotation of the plunger barrel 108 relative to the syringe body 101 whilst allowing translation of the plunger rod assembly 107 relative to the syringe body 101 between the distal and proximal positions.

The plunger barrel 108 may comprise a main body 131. The main body 131 may be generally cylindrical. The main body 131 may be elongate. The main body 131 of the plunger barrel 108 may comprise an internal bore 132. The internal bore 132 may comprise an open end 133 at the proximal end of the internal bore 132 and a closed end 134 at the distal end of the plunger barrel 108. The internal bore 132 may be configured to receive at least a portion of the plunger rod 109.

The plunger barrel 108 may further comprise a first friction fit element 136. The first friction fit element 136 may be configured to engage a second friction fit element 137 located on the plunger 106. The first friction fit element 136 may extend longitudinally from the distal end of the plunger barrel 108. The second friction fit element 137 may be a recess 137 located in the proximal surface of the plunger 106. It will be appreciated that in alternative embodiments, the recess 137 may be located on the plunger barrel 108 and the element 136 may be located on the plunger 106.

At least a section 138 of the internal bore 132 may comprise the second thread 122. In some embodiments, such as the embodiment shown in FIG. 1, the second thread 122 may extend along the length of the internal bore 132. The second thread 122 may be configured to engage the first thread 121 on the plunger rod 109.

The internal bore 132 may further comprise a stop 139. The stop 139 may be configured to cooperate with the plunger rod 109 to prevent the plunger rod 109 from being removed from the internal bore 132 of the plunger barrel 108. The stop 139 may be located at the proximal end of the internal bore 132 of the plunger barrel 108. The stop 139 may be formed by a projection that extend radially inwards from the inner surface of the internal bore 132. The projection 139 may be located in the gap between turns of the second thread 122.

The plunger rod 109 may comprise a shaft 141. The shaft 141 may be configured to be at least partially received in the internal bore 132 of the plunger barrel 108. The shaft 141 may be generally cylindrical. The shaft 141 may be elongate. The shaft 141 may extend parallel to the longitudinal axis X of the medicament delivery device 100.

The shaft 141 may comprise a circumferential outer surface 142. At least a portion 143 of the outer surface 142 of the shaft 141 may comprise the first thread 121. The first thread 121 on at least a portion 142 of the outer surface 142 of the shaft 141 of the plunger rod 109 may be configured to engage the second thread 122 on the inner surface of the internal bore 132 of the plunger barrel 108. In some embodiments, such as the medicament delivery device 100 shown in FIG. 1, the first thread 121 may extend along the whole length of the shaft 141.

The distal end of the shaft 141 may comprise a stop 145. The stop 145 may be configured to cooperate with the stop 139 of the plunger barrel 108 to prevent the plunger rod 109 from being removed from the internal bore 132 of the plunger barrel 108. The stop 145 may be located at the distal end of the shaft 141 of the plunger rod 109. The stop 145 may be formed by a projection that extends radially outwards from the outer surface 142 of the shaft 141. The projection 145 may be located in the gap between turns of the first thread 121.

Each stop 139, 145 may comprise a notch 146 which allows the opposing thread to move through the stop 139, 145 so that relative rotation can be achieved. However, the stops 139, 145 may abut each other to prevent further relative rotation in the second direction when the plunger rod 109 is in its first, maximally extended position.

In some embodiments, the stops 139, 145 may be formed by a ratchet mechanism. The ratchet mechanism may be configured to allow relative rotation of the plunger rod 109 relative to the plunger barrel 108 in the first direction. That is, the ratchet mechanism may be configured to allow relative rotation of the plunger rod 109 relative to the plunger barrel 108 in a direction that results in movement of the plunger rod 109 towards a second position, i.e. distally away from the first position. The ratchet mechanism may be configured to prevent relative rotation of the plunger rod 109 relative to the plunger barrel 108 in the second direction. That is, the ratchet mechanism may be configured to prevent relative rotation of the plunger rod 109 relative to the plunger barrel 108 in a direction that results in movement of the plunger rod 109 towards the first position, i.e. proximally towards the first position. In some embodiments, the stop 145 of the plunger rod 109 may be formed by a series of teeth and the stop 139 on the plunger barrel 108 may be formed by a pawl.

Figure 3:
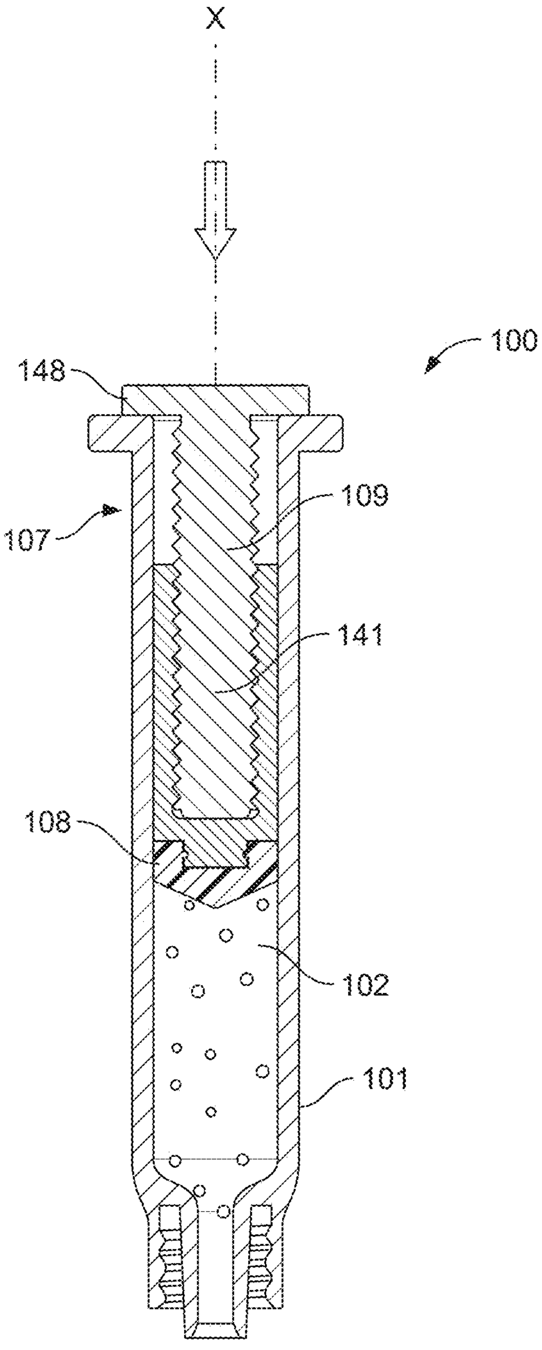
FIG. 3 shows a schematic cross-sectional side view of a medicament delivery device in the second and distal position.

The plunger rod 109 may comprise a head 148. The head 148 may extend from the proximal end of the shaft 141. The head 148 may be generally annular. The head 148 may extend perpendicularly to the longitudinal axis X of the medicament delivery device 100. The head 148 may be configured to abut the proximal end of the syringe body 101 to limit the plunger rod assembly 107 stroke. Thus, a specified dose of medicament may be dispensed when the plunger rod assembly 107 is moved from its proximal position to its distal position, as shown in FIG. 3 and as will be explained in more detail hereinafter.

When the plunger rod assembly 107 is in the proximal position and the plunger rod 109 is in its first position, the distance between the head 148 of the plunger rod 109 and the proximal end of the syringe body 101 is its largest. In this configuration, movement of the plunger rod assembly 107 from the proximal position to the distal position may dispense substantially all of the medicament held in the syringe body 101. However, when the plunger rod assembly 107 is in the proximal position and the plunger rod 109 is rotated relative to the plunger barrel 108 to move the plunger rod 109 into a second, distal position, the distance between the head 148 of the plunger rod 109 and the proximal end of the syringe body 101 is reduced as shown in FIG. 2. The reduction in the distance between the head 148 of the plunger rod 109 and the proximal end of the syringe body 101 reduces the distance that the plunger rod assembly 107, and therefore plunger 106, can be moved in the distal direction. Therefore, the size of the dose that can be dispensed is reduced.

In some embodiments, the distance by which the plunger rod 109 is moved distally from the first position to the second position may be directly proportional to the reduction in the size of the dose of medicament that can be delivered by the medicament delivery device 100.

Figure 4:
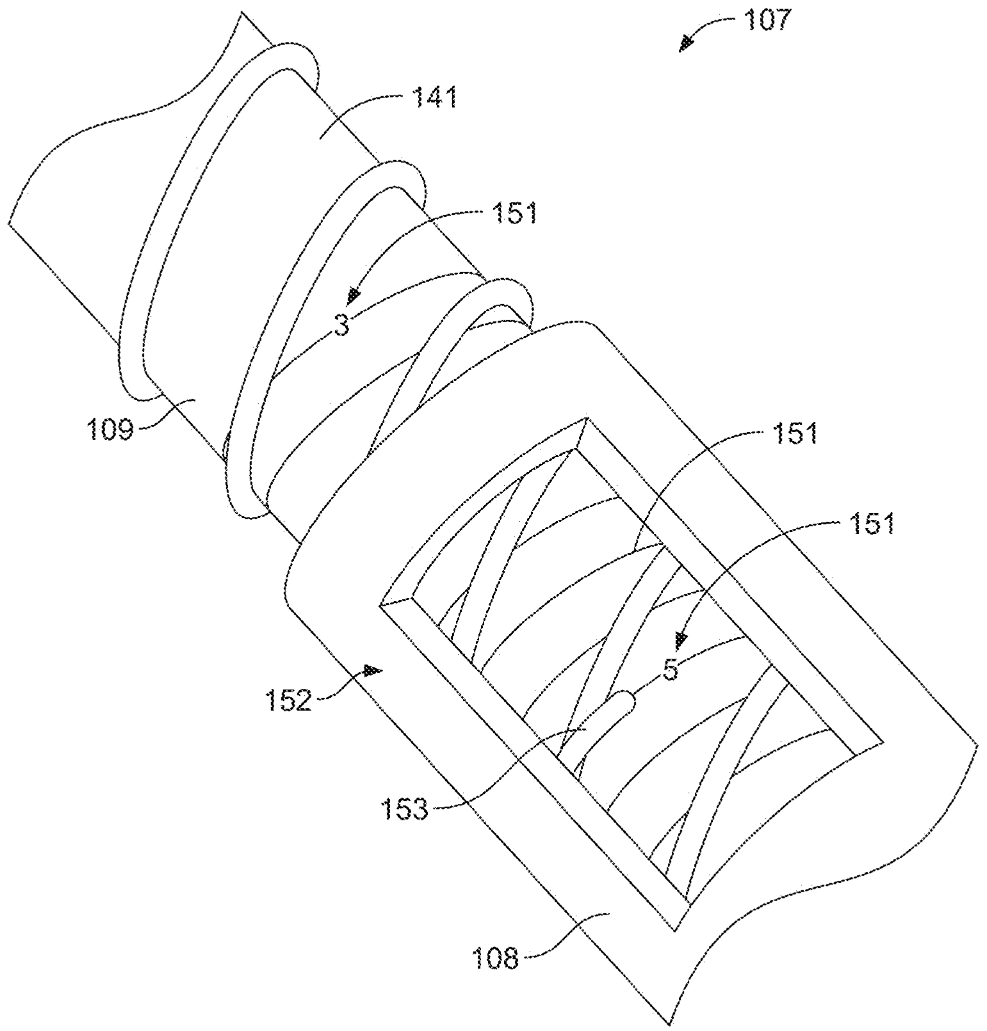
FIG. 4 shows an enlarged schematic side view a plunger rod assembly of the medicament delivery device.

Referring briefly to FIG. 4, a schematic enlarged side view of the plunger rod assembly 107 is shown. The shaft 141 of the plunger rod 109 may comprise a plurality of gradation marks 151. The plurality of graduation marks 151 may be located on the external surface of the shaft 141 of the plunger rod 109. The graduation marks 151 may be configured to indicated to a user the size of the dose set based on the amount of distal movement of the plunger rod 109 relative to the plunger barrel 108 in the distal direction from the first position to a second position. The graduation marks 151 may shown increments of, for example, but not limited to, 0.1 ml to 1 ml. The graduation marks 151 may comprise numbers and/or lines.

Furthermore, the plunger barrel 108 may comprise a window 152. The window 152 may be formed by an aperture that extends from the outer surface of the plunger barrel 108 to the internal bore 132. The window 152 may be located proximate to the proximal end of the plunger barrel 108. The window 152 may be configured to allow a user to see the graduation marks 151 on the shaft 141 of the plunger rod 109 inside the plunger barrel 108. The window may be configured to display the graduation marking 151 that indicate the size of the dose set. The graduation mark 151 indicating the maximum dose may be visible through the window 152 when the plunger rod 109 is in its first, maximally extended position.

The window 152 may further comprise a finger 153. The finger 153 may extend into the window 152. That is, the finger 153 may extend from the periphery of the window 152 towards the centre of the window 152. The finger 153 may be configured to provide a more accurate reading on the graduation marks 151 for determining the size of the dose set.

In an alternative embodiment, the graduation mark 151 that aligns with the proximal end of the plunger barrel 108 may indicate the size of the dose that has been set.

A method of setting a dose of medicament in a medicament delivery device 100 will now be described in reference to FIGS. 1 to 4. The method comprises the step of moving a plunger rod assembly 107 in its first position from a distal position to a proximal position, shown in FIG. 1, to draw medicament into a syringe body 101.

The method further comprises rotating a plunger rod 109 relative to a plunger barrel 108 to move the plunger rod 109 distally from a first position, in which the plunger rod 109 is maximally extended from the plunger barrel 108, to a second position, in which a head 148 of the plunger rod 109 is positioned closer to the distal end 103 of the syringe body 101, to set a specific dose of medicament to be delivered that is less than the amount of medicament received in the syringe body 101.

The method may begin with the plunger rod assembly 107 in the distal position. That is, the plunger rod assembly 107 may be located substantially within the syringe body 101. The head 148 of the plunger rod 109 may abut the proximal end of the syringe body 101. The plunger 106 may be located at the distal end 103 of the syringe body 101. A user may attach a needle to the connecting means 114.

The user may place the distal end of the medicament delivery apparatus 100, i.e. needle, into a container (not shown) storing medicament such that the distal end of the medicament delivery apparatus 100 is submerged in the medicament. The user may then move the plunger rod assembly 107 is the proximal direction. The plunger rod assembly 107 may be moved in the proximal direction by grasping the head 148 of the plunger rod 109 and pulling it away from the syringe body 101. The process of moving the plunger rod assembly 107 in the proximal direction moves the plunger 106 proximally, which creates a vacuum in the syringe body 101 and causes medicament to be drawn into the syringe body 101.

The plunger rod assembly 107 may be moved in the proximal direction until the plunger rod assembly reaches the proximal position. In the proximal position, the plunger rod assembly 107 is at its greatest distance from the distal end 103 of the syringe body 101. During movement of the plunger rod assembly 107 from the distal position to the proximal position, the second cooperating feature 125 on the outer surface of the plunger barrel 108 may move relative to the first cooperating feature 118 on the inner surface of the syringe body 101. That is, the guide channel 125 in the plunger barrel 108 may slide longitudinally past a protrusion 118 of the syringe body 101. Once the plunger barrel 108 has moved to its proximal position, the protrusion 118 may be located at the end of the guide channel 125, where the protrusion 118 acts as a stop 119 by abutting the end of the guide channel 125. The proximal position of the plunger rod assembly 107 and the first position of the plunger rod 109 are shown in FIG. 1.

When the plunger rod assembly 107 is moved to its proximal position, the syringe body 101 may be full of medicament such that the medicament delivery device 100 is capable of delivering a full dose. When the plunger rod assembly 107 is moved into is proximal position, the plunger rod assembly 107 is in its first position. That is, the plunger rod 109 is maximally extended from the plunger barrel 108. At this point, the plunger rod 109 may be rotated in a first direction. Rotation of the plunger rod 109 in the first direction relative to the plunger barrel 108 causes the plunger rod 109 to move in the distal direction due to interaction between the first thread 121 on the plunger rod 109 and the second thread 122 on the plunger barrel 108, as shown in FIG. 2.

Referring to FIG. 4, as the plunger rod 109 is moved from its first position, shown in FIG. 1, to its second position, shown in FIG. 2, the amount of the plunger rod 109 that extends proximally from the plunger barrel 108 is reduced. Graduation marks 151 on the shaft 141 of the plunger rod 109 therefore move in the distal direction. The plunger rod 109 may be rotated until the graduation marks 151 indicate the size of the required dose. The user may stop rotating the plunger rod 109 when the graduation marking 151 indicating the required dose size in shown in a window 152 in the plunger barrel 108 and/or indicated by a finger 153.

Referring to FIG. 3, the user may then move the plunger rod assembly 107 in the distal direction to dispense medicament until the head 148 of the plunger rod 109 contacts the proximal end 104 of the syringe body 101. This contact limits the dose size and prevents and any further medicament being dispensed. The ratchet mechanism may prevent the plunger rod 109 from being moved proximally relative to the plunger rod 109 so that a user cannot attempt to dispense more medicament by adjusting the plunger rod assembly 107. The medicament delivery device 100 may then be disposed of.

Figure 5:
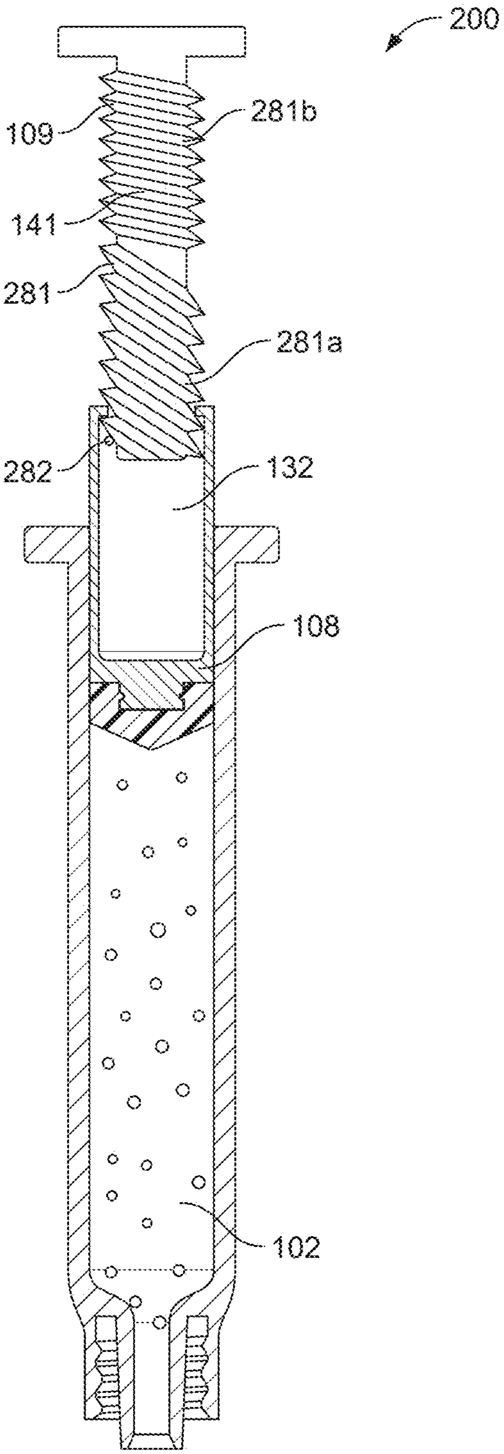
FIG. 5 shows a schematic shows a schematic cross-sectional side view of a medicament delivery device in the first and proximal position.

Referring to FIG. 5, another embodiment of the medicament delivery device 200 is shown. The medicament delivery device 200 illustrated in FIG. 5 is generally the same as the medicament delivery device 100 previously described with reference to FIGS. 1 to 4. Therefore, a detailed description of the medicament delivery device 200 will be omitted herein for the sake of brevity. Furthermore, similar features and components of the embodiment of the medicament delivery device 200 will retain the same terminology and reference numerals.

The main difference between the medicament delivery device 200 of FIG. 5 and the previously described medicament delivery device 100 of FIGS. 1 to 4 is the configuration of the first thread 121 of the plunger rod 109 and the second thread 122 of the plunger barrel 108.

In the medicament delivery device 100, one of the shaft 141 of the plunger rod 109 and the internal bore 132 of the plunger barrel 108 may comprise a thread 281 and the other of the shaft 141 and the internal bore 132 may comprise a protrusion 282 configured to cooperate with the thread 281.

The thread angle of the thread 281 may vary along the length of the shaft 141 of the plunger rod 109 or the internal bore 132 of the plunger barrel 108. For example, the thread angle of the thread 281 on a distal portion of the shaft 141 may be more inclined, i.e. steeper or closer to parallel with the longitudinal axis X, than the thread angle of the thread 281 of a proximal portion of the shaft 141, which is less inclined, i.e. shallower or further from parallel with the longitudinal axis X. Thus, for dose sizes that are small compared to the internal volume of the syringe body 101, the number of rotations of the plunger rod 109 may be reduced to reach a dose size in the vicinity of the required dose size. The shallower thread angle may then be engaged by the protrusion 282, and an accurate dose size can be achieved.

In the present embodiments, the shaft 141 of the plunger rod 109 may comprise the thread 281 and the internal bore 132 of the plunger barrel 108 may comprise a protrusion 282.

As an illustrative example, for a dose of 6.5 ml in a 20 ml syringe body 101, a steeper thread 281*a* may extend over the distal half of the shaft 141 of the plunger rod 109, and a shallower thread 281*b* may extend over the proximal half of the shaft 141. The steeper thread may allow the dose to be reduced by 1 ml per revolution of the plunger rod 109, whereas the shallower thread may allow the dose to be reduced by 0.1 ml per revolution. Thus, the number of turns required to reduce the dose by half may be reduced to 10 turns compared to 100 turns if the shallower thread extended along the full length of the shaft 141 of the plunger rod 109. The number or turns may be adjusted based on the medicament in the apparatus, the dosing of the medicament, or other clinically relevant factors. When the apparatus herein is used with a medicament with comparatively wide therapeutic index, the dose may be increased or decreased by a larger increment. By way of contrast, when the apparatus herein is used with a medicament with comparatively narrow therapeutic index, the dose may be increased or decreased by a smaller increment.

It will be appreciated that the thread 281 may have more than two portions having different thread angles. It will also be appreciated that the different portions of thread angles may extend over any proportion of the shaft 141 of the plunger rod 109, or internal bore 132 of the plunger barrel 108, other than the 50:50 split given in the above example.

The method of setting a dose of medicament in a medicament delivery device 200 is substantially the same as the method previously disclosed in relation to the medicament delivery device 100 illustrated in FIGS. 1 to 4.

Figure 6:
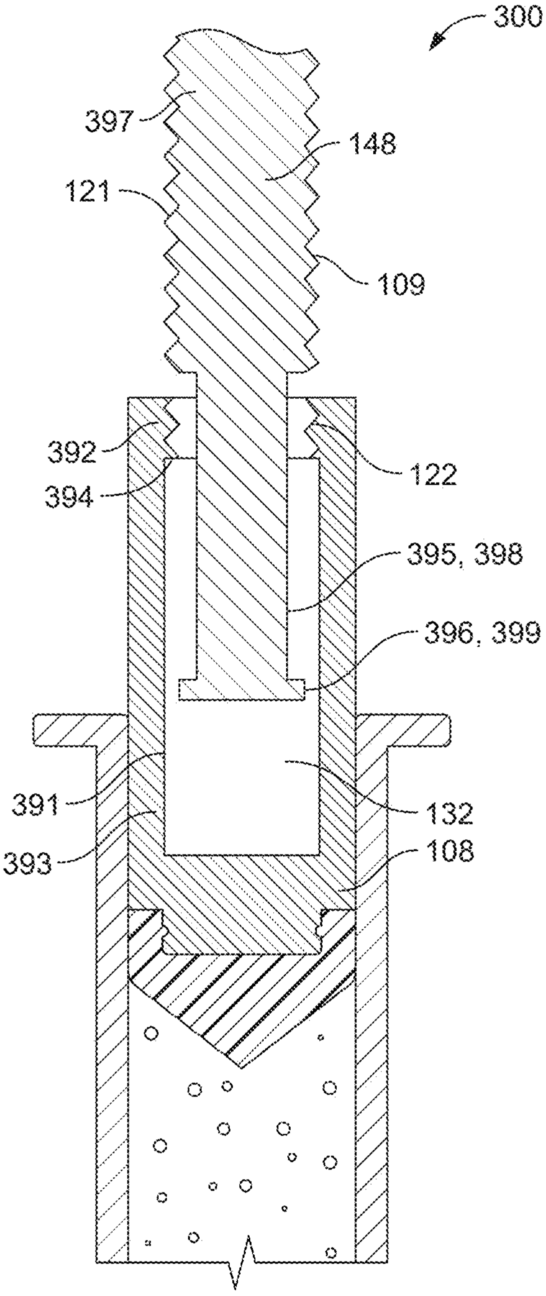
FIG. 6 shows an enlarged schematic shows a schematic cross-sectional side view of a medicament delivery device in the second and proximal position.

Referring to FIG. 6, another embodiment of the medicament delivery device 300 is shown. The medicament delivery device 300 illustrated in FIG. 5 is generally the same as the medicament delivery device 100 previously described with reference to FIGS. 1 to 4. Therefore, a detailed description of the medicament delivery device 300 will be omitted herein for the sake of brevity. Furthermore, similar features and components of the embodiment of the medicament delivery device 300 will retain the same terminology and reference numerals.

The main difference between the medicament delivery device 300 of FIG. 6 and the previously described medicament delivery device 100 of FIGS. 1 to 4 is the configuration of the first thread 121 of the plunger rod 109 and the second thread 122 of the plunger barrel 108.

In the present embodiment, the second thread 122 of the plunger barrel 108 extends along a section of the length of the internal bore 132. More specifically, the second thread 122 of the plunger barrel 108 extends along a proximal section of the length of the internal bore 132 of the plunger barrel 108. That is, the second thread 122 may begin at the proximal end of the internal bore 132 of the plunger barrel 108 and not extend along the full length of the internal bore 132.

The remainder of the length of the internal bore 132 may be formed by a threadless circumferential surface 391. That is, the remainder of the length of the internal bore 132 may be formed by a smooth circumferential surface 391.

In some embodiments, the internal bore 132 of the plunger barrel 108 may comprise a first section 392 and a second section 393. The first section 392 may be located at the proximal end of the internal bore 132. The first section 392 may comprise the second thread 122. The first section 392 may define a narrow section of the internal bore 132. The second section 393 may form the remainder of the internal bore 132, including at least the distal end of the bore 132 and potentially the majority of the proximal end of the internal bore 132 except for the first section 392. The second section 393 may comprise the smooth circumferential surface 391, i.e. threadless surface. The second section 393 may define a wide section of the internal bore 132. The first and second sections 392, 393 may be differentiated by a shoulder 394, which also acts as a stop. The second section 393 of the internal bore 132 may have a wider diameter than the first section 392 of the internal bore 132.

In the present embodiment, the first thread 121 of the plunger rod 109 extends along a section of the length of the plunger rod 109. More specifically, the first thread 121 of the plunger rod 109 extends along a proximal section of the length of the shaft 141 of the plunger rod 109. That is, the first thread 121 may begin at the proximal end of the shaft 141 of the plunger rod 109 and not extend along the full length of the shaft 141.

The remainder of the length of the shaft 141 of the plunger rod 109 may be formed by a threadless circumferential surface 395. That is, the remainder of the length of the shaft 141 may be formed by a smooth circumferential surface 395.

In some embodiments, the shaft 141 may further comprise a stop 396. The stop 396 may be located on the distal end of the shaft 141. The stop 396 may comprise a perpendicularly extending flange. The stop 396 may be an annular flange. The stop 396 may be configured to abut against the shoulder 395 of the plunger barrel 108 when the plunger rod 109 is in its first position.

Therefore, the shaft 141 of the plunger rod 109 may comprise a first section 397, a second section 398, and a third section 399. The first section 397 may be located at at least the proximal end of the shaft 141. The first section 397 may comprise the first thread 121. The diameter of the first section 397 may be dimensioned such that it may cooperate with the first section 392 of the internal bore 132. The third section 399 may be located at the distal end of the shaft 141. The third section 399 may comprise the stop 396. The diameter of the third section 399 may be greater than the diameter of the first section 397 such that it cannot pass through the first section 392 of the plunger barrel 308. The second section 398 of the shaft 141 may extend between the first and third sections 397, 399. The second section 398 may comprise the smooth circumferential surface 395. The second section 398 may have a diameter that is smaller than the diameter of the first section 397 such that it can pass through the first section 392 of the internal bore 132 of the plunger barrel 108.

Thus, in order to reduce the number of turns of the plunger rod 109 the user is required to make to reached the required dose, in the present embodiment the plunger rod 109 may be translated distally relative to the plunger barrel 108 by a distance equal to the length of the second section 398 until the first thread 121 of the first section 397 of the plunger rod 109 engages the second thread 122 of the first section 392 of the plunger barrel 108.

The method of setting a dose of medicament in a medicament delivery device 300 is substantially the same as the method previously disclosed in relation to the medicament delivery device 100 illustrated in FIGS. 1 to 4, except the present embodiment includes the translational distal movement of the plunger rod 109 from the first position before the threads 121, 122 engage and the plunger rod 109 is rotated to cause further distal movement to set the dose required.

It will be appreciated that the syringe body 101 of the medicament delivery device 100, 200, 300 of the present disclosure may be of any suitable size. The syringe body 101 may have a volume of, for example, but not limited to, 5 ml, 10 ml, or 20 ml. The thread pitch of the first and second threads 121, 122 may be matched to the internal volume of the syringe body 101.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about-4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. In some examples, the drugs or medicaments contained in the device as described herein may be used in enzyme replacement therapies or with oncology agents. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N-(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

An example drug delivery device may involve a needle-based injection system as described in Table 1 of section 5.2 of ISO 11608-1:2014 (E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014 (E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014 (E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

| LIST OF REFERENCE NUMERALS | |
|---|---|
| 100 | Medicament Delivery Device |
| 101 | Syringe Body |
| 102 | Medicament |
| 103 | Distal End |
| 104 | Proximal End |
| 106 | Plunger |
| 107 | Plunger Rod Assembly |
| 108 | Plunger Barrel |
| 109 | Plunger Rod |
| 111 | Side Wall |
| 112 | Inner Surface |
| 113 | Distal Opening |
| 114 | Connecting Means |
| 115 | Luer Lock |
| 116 | Proximal Opening |
| 117 | Flange |
| 118 | First Cooperating Feature |
| 119 | Stop |
| 121 | First Thread |
| 122 | Second Thread |
| 125 | Second Cooperating Feature |
| 126 | Stop |
| 131 | Main Body |
| 132 | Internal Bore |
| 133 | Open End |
| 134 | Closed End |
| 136 | First Friction Fit Element |
| 137 | Second Friction Fit Element |
| 139 | Stop |
| 141 | Shaft |
| 142 | Outer Surface |
| 143 | Portion |
| 145 | Stop |
| 146 | Notch |
| 148 | Head |
| 151 | Graduation Marks |
| 152 | Window |
| 153 | Finger |
| 200 | Medicament Delivery Device |
| 281 | Thread |
| 282 | Protrusion |

-continued

| LIST OF REFERENCE NUMERALS | |
|---|---|
| 300 | Medicament Deliver Device |
| 391 | Circumferential Surface |
| 392 | First Section |
| 393 | Second Section |
| 394 | Shoulder |
| 395 | Circumferential Surface |
| 396 | Stop |
| 397 | First Section |
| 398 | Second Section |
| 393 | Third Section |

The invention claimed is:

1. A medicament delivery device comprising:

a syringe body configured to receive a medicament therein, the syringe body comprising a distal end and a proximal end;

a plunger located in and moveable relative to the syringe body; and a plunger rod assembly extending from the proximal end of the syringe body and configured to move the plunger longitudinally within the syringe body, wherein the plunger rod assembly comprises a plunger barrel and a plunger rod, wherein the plunger barrel is in direct contact with the plunger and configured to cooperate with the plunger rod, wherein the plunger rod is moveable relative to the plunger barrel from a first position, in which the plunger rod is maximally extended from the plunger barrel, to a second position, in which the plunger rod is distally away from the first position, to set a specific dose of the medicament to be delivered that is less than an amount of the medicament in the syringe body, wherein the syringe body comprises a protrusion extending radially inward from an inner surface of the syringe body, the protrusion being received in a guide channel of the plunger barrel such that the plunger barrel is rotationally fixed to the syringe body.

2. The medicament delivery device according to claim 1, wherein the plunger rod assembly is moveable between a distal position and a proximal position, and wherein the plunger rod is moveable in a distal direction from the first position to the second position when the plunger rod assembly is in the proximal position.

3. The medicament delivery device according to claim 1, wherein the plunger rod is rotatable relative to the plunger barrel to move the plunger rod from the first position to the second position.

4. The medicament delivery device according to claim 3, wherein the plunger rod comprises a first thread and the plunger barrel comprises a second thread, the first thread and the second thread being configured to cooperate such that when the plunger rod is rotated relative to the plunger barrel, the plunger rod translates distally relative to the plunger barrel.

5. The medicament delivery device according to claim 4, wherein the inner surface of the syringe body comprises a first cooperating feature configured to cooperate with a second cooperating feature on the plunger barrel to prevent relative rotational movement between the plunger barrel and the syringe body.

6. The medicament delivery device according to claim 4, wherein the plunger barrel comprises an internal bore configured to receive at least a portion of the plunger rod, at least a section of the internal bore comprising the second thread configured to engage the first thread on the plunger rod.

7. The medicament delivery device according to claim 6, wherein the second thread extends along a whole length of the internal bore.

8. The medicament delivery device according to claim 6, wherein the second thread extends along a proximal section of a length of the internal bore.

9. The medicament delivery device according to claim 8, wherein the plunger rod comprises a shaft configured to be at least partially received in the internal bore of the plunger barrel, at least a portion of an outer surface of the shaft comprising the first thread configured to engage the second thread on the plunger barrel, and wherein the first thread extends along a proximal portion of a length of the shaft and a distal portion of the shaft comprises a threadless surface.

10. The medicament delivery device according to claim 6, wherein the plunger rod comprises a shaft configured to be at least partially received in the internal bore of the plunger barrel, at least a portion of an outer surface of the shaft comprising the first thread configured to engage the second thread on the plunger barrel.

11. The medicament delivery device according to claim 10, wherein the first thread extends along a whole length of the shaft.

12. The medicament delivery device according to claim 10, wherein a distal end of the shaft comprises a stop configured to abut a projection on a proximal end of the plunger barrel, the shaft and the projection being configured to cooperate to prevent the plunger rod being removed from the plunger barrel.

13. The medicament delivery device according to claim 10, wherein the shaft of the plunger rod comprises a plurality of graduation marks configured to indicate to a user a size of the specific dose set based on an amount of distal movement of the plunger rod relative to the plunger barrel.

14. The medicament delivery device according to claim 13, wherein the plunger barrel comprises a window in which one of the plurality of graduation marks that indicates the size of the specific dose set is displayed.

15. The medicament delivery device according to claim 10, wherein the plunger barrel comprises a finger extending into the window that points towards the one of the plurality of graduation marks that indicates the size of the specific dose set displayed in the window.

16. The medicament delivery device according to claim 3, wherein one of a shaft of the plunger rod and an internal bore of the plunger barrel comprises a thread and the other of the shaft of the plunger rod and the internal bore of the plunger barrel comprises a protrusion configured to cooperate with the thread.

17. The medicament delivery device according to claim 16, wherein a thread angle of the thread varies along a length of the shaft of the plunger rod or the internal bore of the plunger barrel.

18. The medicament delivery device according to claim 1, wherein the plunger rod assembly further comprises a ratchet mechanism configured to allow rotation of the plunger rod relative to the plunger barrel in a direction that results in movement of the plunger rod towards the second position and configured to prevent rotation of the plunger rod relative to the plunger barrel in a direction that results in movement of the plunger rod towards the first position.

19. The medicament delivery device according to claim 1, wherein the plunger rod comprises a head configured to abut the proximal end of the syringe body to limit a stroke of the plunger rod assembly such that the specific dose of the medicament is delivered when the plunger rod assembly is moved from a proximal position to a distal position.

20. The medicament delivery device according to claim 1, wherein the plunger barrel of the plunger rod assembly is configured to move axially relative to the syringe body to eject the medicament.

21. A method of setting a dose of a medicament in a medicament delivery device, the method comprising:

moving a plunger rod assembly of the medicament delivery device from a distal position to a proximal position to draw the medicament into a syringe body of the medicament delivery device; and rotating a plunger rod of the plunger rod assembly relative to a plunger barrel of the plunger rod assembly to move the plunger rod distally from a first position, in which the plunger rod is maximally extended from the plunger barrel, to a second position, in which a head of the plunger rod is positioned closer to a distal end of the syringe body, to set a specific dose of the medicament to be delivered that is less than an amount of the medicament that is in the syringe body, wherein the plunger barrel is in direct contact with a plunger located in and moveable relative to the syringe body, wherein the syringe body comprises a protrusion extending radially inward from an inner surface of the syringe body, the protrusion being received in a guide channel of the plunger barrel such that the plunger barrel is rotationally fixed to the syringe body.

* * * * *